United States Patent
Han et al.

(10) Patent No.: US 11,232,267 B2
(45) Date of Patent: Jan. 25, 2022

(54) PROXIMITY INFORMATION RETRIEVAL BOOST METHOD FOR MEDICAL KNOWLEDGE QUESTION ANSWERING SYSTEMS

(71) Applicant: TENCENT AMERICA LLC, Palo Alto, CA (US)

(72) Inventors: Lianyi Han, Palo Alto, CA (US); Yaliang Li, Santa Clara, CA (US); Zhen Qian, Palo Alto, CA (US); Yusheng Xie, Mountain View, CA (US); Yufan Xue, Palo Alto, CA (US); Tao Yang, Mountain View, CA (US); Wei Fan, New York, NY (US)

(73) Assignee: TENCENT AMERICA LLC, Palo Alto, CA (US)

( * ) Notice: Subject to any disclaimer, the term of this patent is extended or adjusted under 35 U.S.C. 154(b) by 185 days.

(21) Appl. No.: 16/421,554

(22) Filed: May 24, 2019

(65) Prior Publication Data
US 2020/0372117 A1    Nov. 26, 2020

(51) Int. Cl.
*G06F 40/30* (2020.01)
*G06F 40/51* (2020.01)
(Continued)

(52) U.S. Cl.
CPC .......... *G06F 40/51* (2020.01); *G06F 16/9535* (2019.01); *G06F 16/285* (2019.01);
(Continued)

(58) Field of Classification Search
CPC .... G06F 40/211; G06F 40/253; G06F 40/268; G06F 40/284; G06F 40/30; G06F 16/3344
See application file for complete search history.

(56) References Cited

U.S. PATENT DOCUMENTS 9,135,396 B1 *    9/2015    Kalinin ................. G16B 50/00
9,898,424 B2 *    2/2018    van Rooyen .......... G16B 50/00
(Continued)

OTHER PUBLICATIONS

Moen et al., Care episode retrieval: distributional semantic models for information retrieval in the clinical domain, Apr. 2014, The Fifth International Workshop on Health Text Mining and Information Analysis Gothenburg, Sweeden, pp. 1-19. (Year: 2014).*
(Continued)

*Primary Examiner* — Lamont M Spooner
(74) *Attorney, Agent, or Firm* — Sughrue Mion, PLLC

(57) ABSTRACT

A method and apparatus include receiving a first sentence including a first set of words, and a second sentence including a second set of words. A first set of vectors corresponding to the first set of words of the first sentence, and a second set of vectors corresponding to the second set of words of the second sentence are generated using a word embedding model. A similarity matrix based on the first set of vectors and the second set of vectors is generated. An alignment score associated with the first set of vectors and the second set of vectors is determined using the similarity matrix. The alignment score is transmitted to permit information retrieval based on a similarity between the first sentence and the second sentence.

17 Claims, 3 Drawing Sheets

(51) Int. Cl.
*G06F 16/9535* (2019.01)
*G16H 10/20* (2018.01)
*G06F 16/28* (2019.01)
*G06F 40/10* (2020.01)
*G06F 40/58* (2020.01)

(52) U.S. Cl.
CPC .............. *G06F 40/10* (2020.01); *G06F 40/58* (2020.01); *G16H 10/20* (2018.01)

(56) References Cited

U.S. PATENT DOCUMENTS

| | | | |
|---|---|---|---|
| 2007/0150443 A1* | 6/2007 | Bergholz | G06F 16/258 |
| 2007/0189601 A1 | 8/2007 | Lee et al. | |
| 2008/0077570 A1* | 3/2008 | Tang | G06F 16/3346 |
| 2009/0125498 A1* | 5/2009 | Cao | G06F 16/951 |
| 2009/0171955 A1 | 7/2009 | Merz et al. | |
| 2011/0055192 A1* | 3/2011 | Tang | G06F 16/951 |
| | | | 707/706 |
| 2011/0179002 A1 | 7/2011 | Dumitru et al. | |
| 2011/0258736 A1* | 10/2011 | Puzio | C07K 14/195 |
| | | | 800/279 |
| 2013/0344010 A1* | 12/2013 | Pompejus | A23L 33/135 |
| | | | 424/50 |
| 2015/0081657 A1* | 3/2015 | Yi | G06F 16/3338 |
| | | | 707/706 |
| 2015/0379117 A1 | 12/2015 | Kalinin et al. | |
| 2018/0246915 A1* | 8/2018 | Singh | G06F 16/221 |
| 2019/0347281 A1* | 11/2019 | Natterer | G06F 16/3344 |
| 2020/0175015 A1* | 6/2020 | Al Hasan | G06N 3/08 |

OTHER PUBLICATIONS

Moen, Distributional Semantic Models for Clinical Text Applied to Health Record Summarization, 2016, NTNU, pp. 1-188. (Year: 2016).*

Written Opinion in International Application No. PCT/US2020/025201, dated Jun. 19, 2020.

International Search Report in International Application No. PCT/US2020/025201, dated Jun. 19, 2020.

* cited by examiner

PROXIMITY INFORMATION RETRIEVAL BOOST METHOD FOR MEDICAL KNOWLEDGE QUESTION ANSWERING SYSTEMS

BACKGROUND

A question answering (QA) system is a system designed to answer questions posed in available information such as image, video, voice, and natural language. As an example, a medical QA system draws information from unified biomedical literature and aims to answer medical related questions. Continuing the example, the knowledgebase is focused on biomedical resources, and questions and answers are expressed in Mandarin full text. Resolving QA problems requires several fundamental abilities including information retrieval (IR), reasoning, memorization etc., and the most encountered and arguably the most critical step is the IR step. For instance, the task is to select the most relevant references from millions of documents in the knowledgebase. Often, the problem is not due to limited biomedical resources, but instead due to deficiencies associated with ranking, and identifying from among millions of available resources, the most relevant resources in the context of the question and answer.

One of the full text search engines, Lucene (KeywordAnalyzer "Better Search with Apache Lucene and Solr". 19 Nov. 2007), has been widely recognized to implement recommendation systems (McCandless, Michael; Hatcher, Erik; Gospodnetié, Otis (2010). Lucene in Action, Second Edition. Manning. p. 8. ISBN 193398817). The power of the inverted index and the term frequency-inverse document frequency (TF-IDF) derived relevance ranking, such as Okapi BM25, demonstrated to be able to rank documents based on query terms as in a bag of words (BOW) approach, regardless of the inter-relationship between the matching terms within a document. This BOW approach has been a feature, where the search can be implemented efficiently based on a cosine model, while it can also rank the documents reasonably well in many recommendation systems. However, it also has its own drawbacks. One use case is regarding when to search two similar sentences with nearly identical BOW but different contextual meanings. It can be increasingly difficult to distinguish them based solely on the relevance scores. To tackle this problem towards a better IR component in the biomedical QA systems, this disclosure provides an enhanced proximity search extended from on ElasticSearch/Lucene index.

SUMMARY

According to an aspect of the disclosure, a method for performing information retrieval using sentence similarity, includes receiving, by a device, a first sentence including a first set of words; receiving, by the device, a second sentence including a second set of words; generating, by the device and using a word embedding model, a first set of vectors corresponding to the first set of words of the first sentence; generating, by the device and using the word embedding model, a second set of vectors corresponding to the second set of words of the second sentence; generating, by the device, a similarity matrix based on the first set of vectors and the second set of vectors; determining, by the device, an alignment score associated with the first set of vectors and the second set of vectors using the similarity matrix; and transmitting, by the device, the alignment score to permit information retrieval based on a similarity between the first sentence and the second sentence.

According to an aspect of the disclosure, a device includes at least one memory configured to store program code; at least one processor configured to read the program code and operate as instructed by the program code, the program code includes receiving code configured to cause the at least one processor to receive a first sentence including a first set of words, and receive a second sentence including a second set of words; generating code configured to cause the at least one processor to generate, using a word embedding model, a first set of vectors corresponding to the first set of words of the first sentence, generate, using the word embedding model, a second set of vectors corresponding to the second set of words of the second sentence, and generate a similarity matrix based on the first set of vectors and the second set of vectors; determining code configured to cause the at least one processor to determine an alignment score associated with the first set of vectors and the second set of vectors using the similarity matrix; and transmitting code configured to cause the at least one processor to transmit the alignment score to permit information retrieval based on a similarity between the first sentence and the second sentence.

According to an aspect of the disclosure, a non-transitory computer-readable medium stores instructions, the instructions comprising: one or more instructions that, when executed by one or more processors of a device, cause the one or more processors to: receive, by a device, a first sentence including a first set of words; receive, by the device, a second sentence including a second set of words; generate, by the device and using a word embedding model, a first set of vectors corresponding to the first set of words of the first sentence; generate, by the device and using the word embedding model, a second set of vectors corresponding to the second set of words of the second sentence; generate, by the device, a similarity matrix based on the first set of vectors and the second set of vectors; determine, by the device, an alignment score associated with the first set of vectors and the second set of vectors using the similarity matrix; and transmit, by the device, the alignment score to permit information retrieval based on a similarity between the first sentence and the second sentence.

DETAILED DESCRIPTION

Figure 1:
FIG. 1 is a flow chart of an example process described herein.

Recent advances in natural language processing (NLP) and IR techniques have promoted the analysis of large scale digital biomedical information such as image, text, clinical and genetic data. The progress in biomedical NLP, such as term entity recognition (Kim S, Lu Z, Wilbur W J. Identifying named entities from PubMed for enriching semantic categories. BMC Bioinformatics. 2015 Feb. 21; 16:57), the availability of inverted index search engine, such as Lucene[2], and distributable column based storage systems and analytical databases, such as BigTable (Chang, Fay; Dean, Jeffrey; Ghemawat, Sanjay; et al (2006), "Bigtable: A Distributed Storage System for Structured Data", Google.) and ElasticSearch (https://www.elastic.co/), have made biomedical searching even more powerful to process billions of documents, support high concurrent queries, and return the document relevance related to the queries.

The IR component of the biomedical QA system of the present disclosure was engineered with the above mentioned features on the top of ElasticSearch and Lucene index, where the queries and documents can be analyzed by stemming, performing stop word analysis, and performing synonymous expansion. However, one noticeable issue is due to the BOW searching strategy of the boolean queries in the Lucene Index, where the proximity of the two matching documents are not easily and directly reflected by the relevancy score.

Due to the complex nature of the language and the high volume of documents, the full text content may contains similar bag of words, while their contextual difference may be significantly different. On the other hand, the interpretation of the sentence becomes increasingly important to understand the meaning of the text, and this is especially critical in a QA system. Below is an example given in Mandarin:

1. 医疗机构内发现甲 类传染病时对疑似 病人确诊前在指定 场所单独隔离治疗; (When a Class A infectious disease is found in a medical institution, the suspected patient shall be isolated and treated in a designated place before the diagnosis is confirmed.)

2. 发现甲类传染病是 处于医疗机构 内的病人、病原携带者、疑似病人的密切 接触者 在指 定场所进行医 学观察和采取其他 必要的预防措施。 (It is discovered that the Type A infectious diseases are close contacts of patients, pathogen carriers, and suspected patients in medical institutions. Medical observations and other necessary preventative measures are taken in designated places.)

If the question is to ask the what would be a better answer by query/question: 医疗机构 内发现甲类传染病疑 似病人的措施 (measures to detect suspected patients of Class A infectious diseases in medical institutions) and the two possible answers are 单独隔离治疗 (isolated treatment) and 医学观察 (medical observation), it would be difficult to tell which one is correct based solely on default scoring since the search terms of the query/question are very close to the terms of both sentences 1 and 2 above and similar in terms of their bag of words presentation. The proximity search using the span query might be helpful, however that requires the terms from both queries to contain all of the query terms, which is criteria often not meet in a full text search. In this disclosure, a post processing step was added to analyze the span of the terms groups among the returned matched documents, and rank the marched documents based on the proximity of the terms.

The proposed disclosure can be used to boost the IR component in a biomedical QA system for selecting the most relevant and representative references for usage with attention and predictive models. The effectiveness and enrichment of this IR component are important for concept interpretation of the QA system. The relevancy ranking is a significant factor to evaluate the significance of the references accountable for understanding a question and correlating its concept to the correct answer. This disclosure provides a relevancy ranking based on the proximity of the full text of the question relative to the full text of the answers, so to retrieve the references as close to the QA as possible.

The full text of the questions and answers are analyzed through NLP processes where tokenization and synonymous expansion occur during the Elastic Search indexing time. The full text was tokenized based on bigram and trigram, stop word analysis was applied after tokenization, and the acronyms were expanded thereafter. The acronyms and dictionary were based on 词林同义 (https://github.com/BiLiangLtd/WordSimilarity/blob/master/data/cilin_ex.txt) and further extended by modeling about 300,000 documents collected from nearly 100 biomedical literature resources. The title and the full content of the literature were concatenated to reduce the gap between terms across the title and content.

The word vectorization is an important step to measure the similarities between words, prior to tuning the similarities of sentences. The present disclosure provides a word2vec (https://code.google.com/archive/p/word2vec/) implementation of the continuous bag-of-words and skip-gram architectures for computing vector representations of words. The similarities of two words thus can be measured by the cosine similarity (https://en.wikipedia.org/wiki/Cosine_similarity):

$$\text{similarity} = \cos(\theta) = \frac{A \cdot B}{\|A\|\|B\|} = \frac{\sum_{i=1}^{n} A_i B_i}{\sqrt{\sum_{i=1}^{n} A_i^2} \sqrt{\sum_{i=1}^{n} B_i^2}},$$

The value is between 0 and 1, where a value closer to 1 indicates that the words are more similar.

One way of measuring the string similarity is to measure their Edit distance by counting the minimum number of operations required to transform one string into the other. For example, the Levenshtein distance (https://en.wikipedia.org/wiki/Levenshtein_distance) measures the operations including removal, insertion, or substitution of a character in the string. In the case of full text similarities that might have hundreds of words spanning multiple sentences, and where the compared sentences might not have good word identify coverage, editing distance may be less informative compared to the TF-IDF. This disclosure proposes a refined Needleman-Wunsch algorithm, that uses dynamic programming to align two sentences, with the score of substitution uses the cosine score of the word2vec representation.

The following pseudo-code for the algorithm was adopted and modified from the original implementation (https://en.wikipedia.org/wiki/Needleman%E2%80%93Wunsch_algorithm), where an F matrix is the matrix to hold the alignment scores of two list of words. F(i,j) is the score of the two words matching/mismatching scores (each word from different sentence). A and B are the vectors of words from two sentences for comparison. "Similarity" function took the vector representation of two words for computing a cosine similarity. The algorithm contains a forward pass and a backward pass over the F matrix.

The forward pass is to compute the F matrix:
```
d←−1 #mismatched/indel score is −1
for i=0 to length(A)
    F(i,0)←d*i
for j=0 to length(B)
    F(0,j)←d*j
for i=1 to length(A)
    for j=1 to length(B)
```

Match←F(i−1,j−1)+Similarity(word2vec(A$_i$), (B$_j$))
Delete←F(i−1, j)+d
Insert←F(i, j−1)+d
F(i,j)←max(Match, Insert, Delete)

Once the F matrix is computed, the backward pass is to assemble the alignment by starting from the bottom right cell, and compare the value of three possible movement direction(top, left, top-left diagonal), to see which passage gives the best score:

```
AlignmentA ← ""
AlignmentB ← ""
Score ← 0
IdentityScore ← 0
i ← length(A)
j ← length(B)
while (i > 0 or j > 0)
    Score ← Score+F(i,j)
    if (i > 0 and j > 0 and F(i,j) == F(i−1 ,j−1) +
    Similarity(word2vec(A_i), (B_j)))
        AlignmentA ← A_i + AlignmentA
AlignmentB ← B_j + AlignmentB
Identity Score++
        i−−
        j−−
    else if (i > 0 and F(i,j) == F(i−1,j) + d)
        AlignmentA ← A_i + AlignmentA
        AlignmentB ← "−" + AlignmentB # gap added to B
        i−−
    else
        AlignmentA ← "−" + AlignmentA # gap added to A
        AlignmentB ← B_j + AlignmentB
        j−−
}
IdentityScore ← IdentityScore/len(AlignmentA)
```

The cumulative score "score"([0,1]) and the IdentityScore ([0,1]) can be used to evaluate the sentence similarities.

In this way, the extension of the TF-IDF based relevance score using the proposed proximity search allows the documents ranked higher to reflect their contextual similarity.

The similarities among tokens are not limited to the exact substitution, but their proximity meaning (the word2vec approach), that bring the full text interpretation closer to its meaning for facilitating the QA systems The up-weighting of the proximity matching over the extract term matching allows the more diverse documents ranked on the top, that increases the representativeness of the retrieved documents for the downstream medical QA system processing.

FIG. 1 is a flow chart of an example process 100 according to an aspect of the disclosure.

As shown in FIG. 1, process 100 may include receiving, by a device, a first sentence including a first set of words (block 110).

As further shown in FIG. 1, process 100 may include receiving, by the device, a second sentence including a second set of words (block 120).

As further shown in FIG. 1, process 100 may include generating, by the device and using a word embedding model, a first set of vectors corresponding to the first set of words of the first sentence (block 130).

As further shown in FIG. 1, process 100 may include generating, by the device and using the word embedding model, a second set of vectors corresponding to the second set of words of the second sentence (block 140).

As further shown in FIG. 1, process 100 may include generating, by the device, a similarity matrix based on the first set of vectors and the second set of vectors (block 150).

As further shown in FIG. 1, process 100 may include determining, by the device, an alignment score associated with the first set of vectors and the second set of vectors using the similarity matrix (block 160).

As further shown in FIG. 1, process 100 may include determining whether the alignment score is a maximum alignment score (block 170).

As further shown in FIG. 1, if the alignment score is not a maximum alignment score (block 170—NO), then process 100 may include determining another alignment score based on a different direction of the similarity matrix (block 180).

As further shown in FIG. 1, if the alignment score is the maximum alignment score (block 170—YES), then process 100 may include transmitting, by the device, the alignment score to permit information retrieval based on a similarity between the first sentence and the second sentence (block 190).

Figure 2:
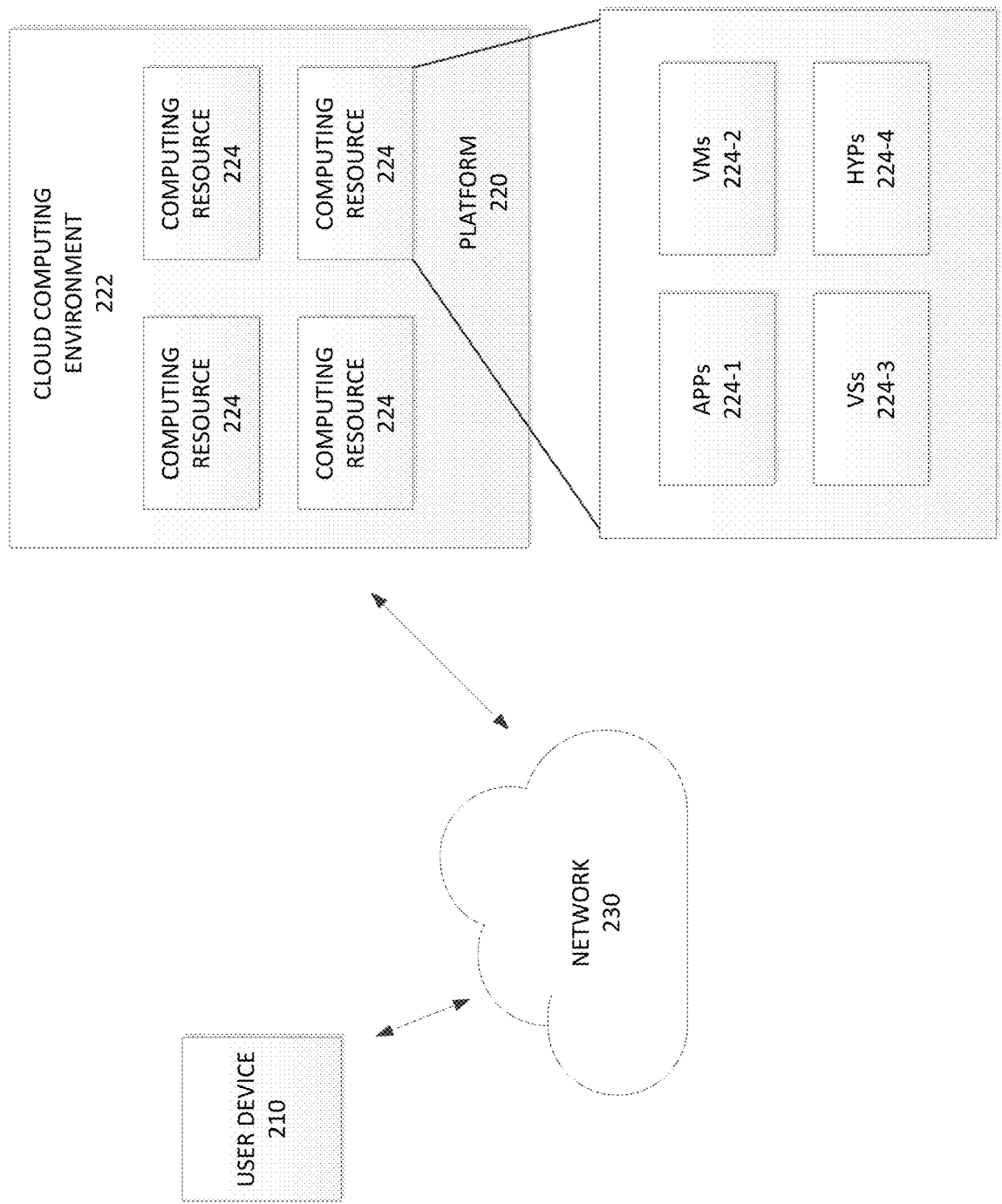
FIG. 2 is a diagram of an example environment in which systems and/or methods, described herein, may be implemented.

In some implementations, one or more process blocks of FIG. 1 may be performed by platform 220 as described in association with FIG. 2. In some implementations, one or more process blocks of FIG. 1 may be performed by another device or a group of devices separate from or including platform 220, such as user device 210.

Although FIG. 1 shows example blocks of process 100, in some implementations, process 100 may include additional blocks, fewer blocks, different blocks, or differently arranged blocks than those depicted in FIG. 1. Additionally, or alternatively, two or more of the blocks of process 400 may be performed in parallel.

FIG. 2 is a diagram of an example environment 200 in which systems and/or methods, described herein, may be implemented. As shown in FIG. 2, environment 200 may include a user device 210, a platform 220, and a network 230. Devices of environment 200 may interconnect via wired connections, wireless connections, or a combination of wired and wireless connections.

User device 210 includes one or more devices capable of receiving, generating, storing, processing, and/or providing information associated with platform 220. For example, user device 210 may include a computing device (e.g., a desktop computer, a laptop computer, a tablet computer, a handheld computer, a smart speaker, a server, etc.), a mobile phone (e.g., a smart phone, a radiotelephone, etc.), a wearable device (e.g., a pair of smart glasses or a smart watch), or a similar device. In some implementations, user device 210 may receive information from and/or transmit information to platform 220.

Platform 220 includes one or more devices capable of identification of bug bites using artificial intelligence (AI) techniques, as described elsewhere herein. In some implementations, platform 220 may include a cloud server or a group of cloud servers. In some implementations, platform 220 may be designed to be modular such that certain software components may be swapped in or out depending on a particular need. As such, platform 220 may be easily and/or quickly reconfigured for different uses.

In some implementations, as shown, platform 220 may be hosted in cloud computing environment 222. Notably, while implementations described herein describe platform 220 as being hosted in cloud computing environment 222, in some implementations, platform 220 is not be cloud-based (i.e., may be implemented outside of a cloud computing environment) or may be partially cloud-based.

Cloud computing environment 222 includes an environment that hosts platform 220. Cloud computing environment 222 may provide computation, software, data access, storage, etc. services that do not require end-user (e.g., user device 210) knowledge of a physical location and configuration of system(s) and/or device(s) that hosts platform 220. As shown, cloud computing environment 222 may include a group of computing resources 224 (referred to collectively as "computing resources 224" and individually as "computing resource 224").

Computing resource 224 includes one or more personal computers, workstation computers, server devices, or other types of computation and/or communication devices. In some implementations, computing resource 224 may host platform 220. The cloud resources may include compute instances executing in computing resource 224, storage devices provided in computing resource 224, data transfer devices provided by computing resource 224, etc. In some implementations, computing resource 224 may communicate with other computing resources 224 via wired connections, wireless connections, or a combination of wired and wireless connections.

As further shown in FIG. 2, computing resource 224 includes a group of cloud resources, such as one or more applications ("APPs") 224-1, one or more virtual machines ("VMs") 224-2, virtualized storage ("VSs") 224-3, one or more hypervisors ("HYPs") 224-4, or the like.

Application 224-1 includes one or more software applications that may be provided to or accessed by user device 210 and/or sensor device 220. Application 224-1 may eliminate a need to install and execute the software applications on user device 210. For example, application 224-1 may include software associated with platform 220 and/or any other software capable of being provided via cloud computing environment 222. In some implementations, one application 224-1 may send/receive information to/from one or more other applications 224-1, via virtual machine 224-2.

Virtual machine 224-2 includes a software implementation of a machine (e.g., a computer) that executes programs like a physical machine. Virtual machine 224-2 may be either a system virtual machine or a process virtual machine, depending upon use and degree of correspondence to any real machine by virtual machine 224-2. A system virtual machine may provide a complete system platform that supports execution of a complete operating system ("OS"). A process virtual machine may execute a single program, and may support a single process. In some implementations, virtual machine 224-2 may execute on behalf of a user (e.g., user device 210), and may manage infrastructure of cloud computing environment 222, such as data management, synchronization, or long-duration data transfers.

Virtualized storage 224-3 includes one or more storage systems and/or one or more devices that use virtualization techniques within the storage systems or devices of computing resource 224. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 224-4 may provide hardware virtualization techniques that allow multiple operating systems (e.g., "guest operating systems") to execute concurrently on a host computer, such as computing resource 224. Hypervisor 224-4 may present a virtual operating platform to the guest operating systems, and may manage the execution of the guest operating systems. Multiple instances of a variety of operating systems may share virtualized hardware resources.

Network 230 includes one or more wired and/or wireless networks. For example, network 230 may include a cellular network (e.g., a fifth generation (5G) network, a long-term evolution (LTE) network, a third generation (3G) network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, or the like, and/or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
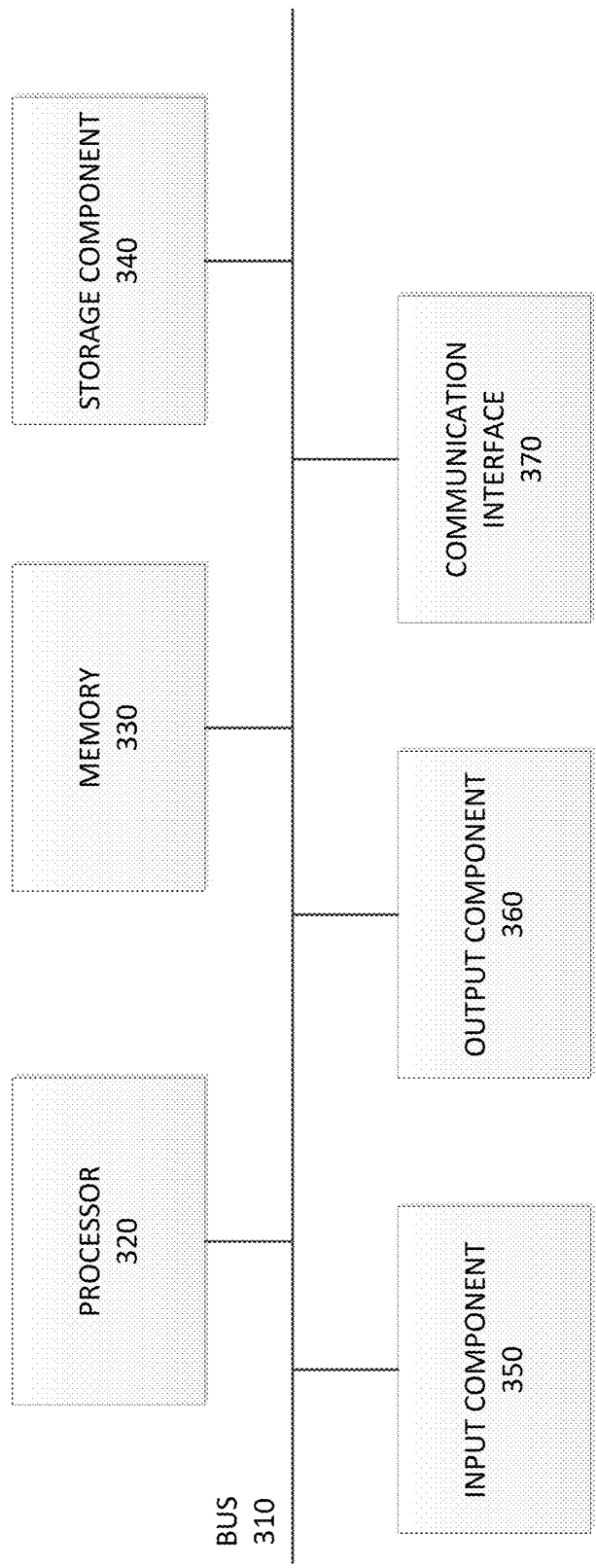
FIG. 3 is a diagram of example components of one or more devices of FIG. 2.

FIG. 3 is a diagram of example components of a device 300. Device 300 may correspond to user device 210 and/or platform 220. As shown in FIG. 3, device 300 may include a bus 310, a processor 320, a memory 330, a storage component 340, an input component 350, an output component 360, and a communication interface 370.

Bus 310 includes a component that permits communication among the components of device 300. Processor 320 is implemented in hardware, firmware, or a combination of hardware and software. Processor 320 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, and/or an actuator). Output component 360 includes a component that provides output information from device 300 (e.g., a display, a speaker, and/or one or more light-emitting diodes (LEDs)).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, or the like.

Device 300 may perform one or more processes described herein. Device 300 may perform these processes in response to processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, or a combination of hardware and software.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware may be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A method for performing information retrieval using sentence similarity, the method comprising:
   receiving, by a device, a first sentence including a first set of words;
   receiving, by the device, a second sentence including a second set of words;
   generating, by the device and using a word embedding model, a first set of vectors corresponding to the first set of words of the first sentence;
   generating, by the device and using the word embedding model, a second set of vectors corresponding to the second set of words of the second sentence;
   determining, by the device, a cosine similarity of words of the first sentence and the second sentence, based on the first set of vectors and the second set of vectors;
   determining, by the device, a string similarity between the first sentence and the second sentence by computing a Needleman-Wunsch matrix, based on the first set of vectors, the second set of vectors, and the cosine similarity, the computed Needleman-Wunsch matrix holding alignment scores for alignments of the first set of vector and the second set of vectors, the string similarity being based on the alignment scores; and
   transmitting, by the device, the string similarity to permit the information retrieval.

2. The method of claim 1, further comprising:
   performing a backward pass over the computed Needleman-Wunsch matrix by starting from a bottom right cell of the Needleman-Wunsch matrix and comparing the alignment scores associated with a set of possible movement directions to find a passage through the Needleman-Wunsch matrix that provides a best alignment score.

3. The method of claim 2, wherein the set of possible movement directions includes a top direction, a left direction, and a left diagonal direction based on the bottom right cell of the Needleman-Wunsch matrix.

4. The method of claim 2, further comprising:
   evaluating a sentence similarity between the first sentence and the second sentence based on the best alignment score.

5. The method of claim 1, wherein the word embedding model is a word2vec model.

6. The method of claim 1, wherein the information retrieval is for providing answers to questions, and the first sentence is a question for the information retrieval and the second sentence is an answer to the question.

7. The method of claim 6, further comprising ranking the second sentence based on the string similarity.

8. A device, comprising:
   at least one memory configured to store program code;
   at least one processor configured to read the program code and operate as instructed by the program code, the program code including:
   receiving code configured to cause the at least one processor to receive a first sentence including a first set of words, and receive a second sentence including a second set of words;
   generating code configured to cause the at least one processor to generate, using a word embedding model, a first set of vectors corresponding to the first set of words of the first sentence, generate, using the word embedding model, a second set of vectors corresponding to the second set of words of the second sentence;
   determining code configured to cause the at least one processor to determine a cosine similarity of words of the first sentence and the second sentence, based on the first set of vectors and the second set of vectors, and determine a string similarity between the first sentence and the second sentence by computing a Needleman-Wunsch matrix, based on the first set of vectors, the second set of vectors, and the cosine similarity, the computed Needleman-Wunsch matrix holding alignment scores for alignments of the first set of vector and the second set of vectors, the string similarity being based on the alignment scores; and
   transmitting code configured to cause the at least one processor to transmit the string similarity to permit the information retrieval.

9. The device of claim 8, further comprising:
   comparing code configured to cause the at least one processor to perform a backward pass over the computed Needleman-Wunsch matrix by starting from a bottom right cell of the Needleman-Wunsch matrix and compare the alignment scores associated with a set of possible movement directions to find a passage through the Needleman-Wunsch matrix that provides a best alignment score.

10. The device of claim 9, wherein the set of possible movement directions includes a top direction, a left direction, and a left diagonal direction based on the bottom right cell of the Needleman-Wunsch matrix.

11. The device of claim 9, further comprising:
   evaluating code configured to cause the at least one processor to evaluate a sentence similarity between the first sentence and the second sentence based on the best alignment score.

12. The device of claim 8, wherein the word embedding model is a word2vec model.

13. A non-transitory computer-readable medium storing instructions, the instructions comprising: one or more instructions that, when executed by one or more processors of a device, cause the one or more processors to at least:
   receive a first sentence including a first set of words;
   receive a second sentence including a second set of words;
   generate, using a word embedding model, a first set of vectors corresponding to the first set of words of the first sentence;
   determine a cosine similarity of words of the first sentence and the second sentence, based on the first set of vectors and the second set of vectors;
   determine a string similarity between the first sentence and the second sentence by computing a Needleman-Wunsch matrix, based on the first set of vectors, the second set of vectors, and the cosine similarity, the computed Needleman-Wunsch matrix holding alignment scores for alignments of the first set of vector and the second set of vectors, the string similarity being based on the alignment scores; and
   transmit the string similarity to permit the information retrieval.

14. The non-transitory computer-readable medium of claim 13, wherein the one or more instructions are further configured to cause the one or more processors to:
   perform a backward pass over the computed Needleman-Wunsch matrix by starting from a bottom right cell of the Needleman-Wunsch matrix and comparing the alignment scores associated with a set of possible movement directions to find a passage through the Needleman-Wunsch matrix that provides a best alignment score.

15. The non-transitory computer-readable medium of claim 14, wherein the set of possible movement directions includes a top direction, a left direction, and a left diagonal direction based on a bottom right cell of the Needleman-Wunsch matrix.

16. The non-transitory computer-readable medium of claim 14, wherein the one or more instructions are further configured to cause the one or more processors to:
   evaluate a sentence similarity between the first sentence and the second sentence based on the best alignment score.

17. The non-transitory computer-readable medium of claim 13, wherein the word embedding model is a word2vec model.

* * * * *